US012751664B2

(12) United States Patent
Valkonen et al.

(10) Patent No.: US 12,751,664 B2
(45) Date of Patent: Oct. 6, 2026

(54) SNORING AND ENVIRONMENT SOUNDS DETECTION

(71) Applicant: Oura Health Oy, Oulu (FI)

(72) Inventors: Miska Mikael Viljami Valkonen, Jyväskylä (FI); Robert Alexander Singleton, Toronto (CA); Antti Oskari Laitala, Oulu (FI); Dmitry Sergeev, Helsinki (FI); Harry Tily, London (GB); Matias Valtteri Kukka, Tampere (FI); Mats Kyyrö, Oulu (FI)

(73) Assignee: Oura Health Oy, Oulu (FI)

( * ) Notice: Subject to any disclaimer, the term of this patent is extended or adjusted under 35 U.S.C. 154(b) by 418 days.

(21) Appl. No.: 18/455,048

(22) Filed: Aug. 24, 2023

(65) Prior Publication Data

US 2025/0064386 A1 Feb. 27, 2025

(51) Int. Cl.
*A61B 5/00* (2006.01)
*A61B 7/00* (2006.01)

(52) U.S. Cl.
CPC .......... *A61B 5/4809* (2013.01); *A61B 5/6802* (2013.01); *A61B 5/7282* (2013.01); *A61B 5/743* (2013.01); *A61B 7/003* (2013.01)

(58) Field of Classification Search
CPC ... A61B 5/4809; A61B 5/6802; A61B 5/7282; A61B 5/743; A61B 7/003; A61B 5/4815
See application file for complete search history.

(56) References Cited

U.S. PATENT DOCUMENTS

2006/0212273 A1* 9/2006 Krausman ............ A61B 5/4818 702/189
2012/0071741 A1* 3/2012 Moussavi .............. A61B 7/003 600/340
2015/0164238 A1* 6/2015 Benson ................ A61B 5/6892 340/540
2016/0015314 A1* 1/2016 Dusanter .............. A61B 5/4818 600/301
2016/0015315 A1* 1/2016 Auphan ............... A61B 5/7435 600/587
2019/0038185 A1* 2/2019 Arnold ................. A61B 5/7278
2022/0133221 A1* 5/2022 Lawlor .................. G16H 50/30 600/300
2022/0346705 A1* 11/2022 Taki ....................... A61B 7/003
2023/0173221 A1* 6/2023 Shouldice .............. G16H 20/40 600/26

* cited by examiner

*Primary Examiner* — Ryan W Sherwin
(74) *Attorney, Agent, or Firm* — ArentFox Schiff LLP

(57) ABSTRACT

Methods, systems, and devices for evaluating a sleep quality of a user using wearable-based data are described. The sleep quality of a user may be evaluated by combining physiological data collected via a wearable device, along with environmental sound data collected via one or more external devices. For example, a microphone on a device may monitor environmental sounds while a user sleeps, and the environmental sounds may be used to improve sleep stage classification. Additionally, or alternatively, sound instances occurring throughout a sleep interval may be identified. In some examples, sound data may be combined with other data, such as physiological data, to determine relationships between the sleep sound data and sleep quality. An indication of the sleep stages and transitions between the sleep stages, the sound instances, the sleep quality, or a combination thereof, may be presented to the user via an application.

18 Claims, 6 Drawing Sheets

SNORING AND ENVIRONMENT SOUNDS DETECTION

FIELD OF TECHNOLOGY

The following relates to wearable devices and data processing, including techniques for snoring and environmental sounds detection.

BACKGROUND

Wearable devices may be configured to collect physiological data from users, such as heart rate data, heart rate variability (HRV) data, movement data, and other information about the user. In some examples, there may be a correlation between the physiological data and a user's sleep quality.

DETAILED DESCRIPTION

Figure 1:
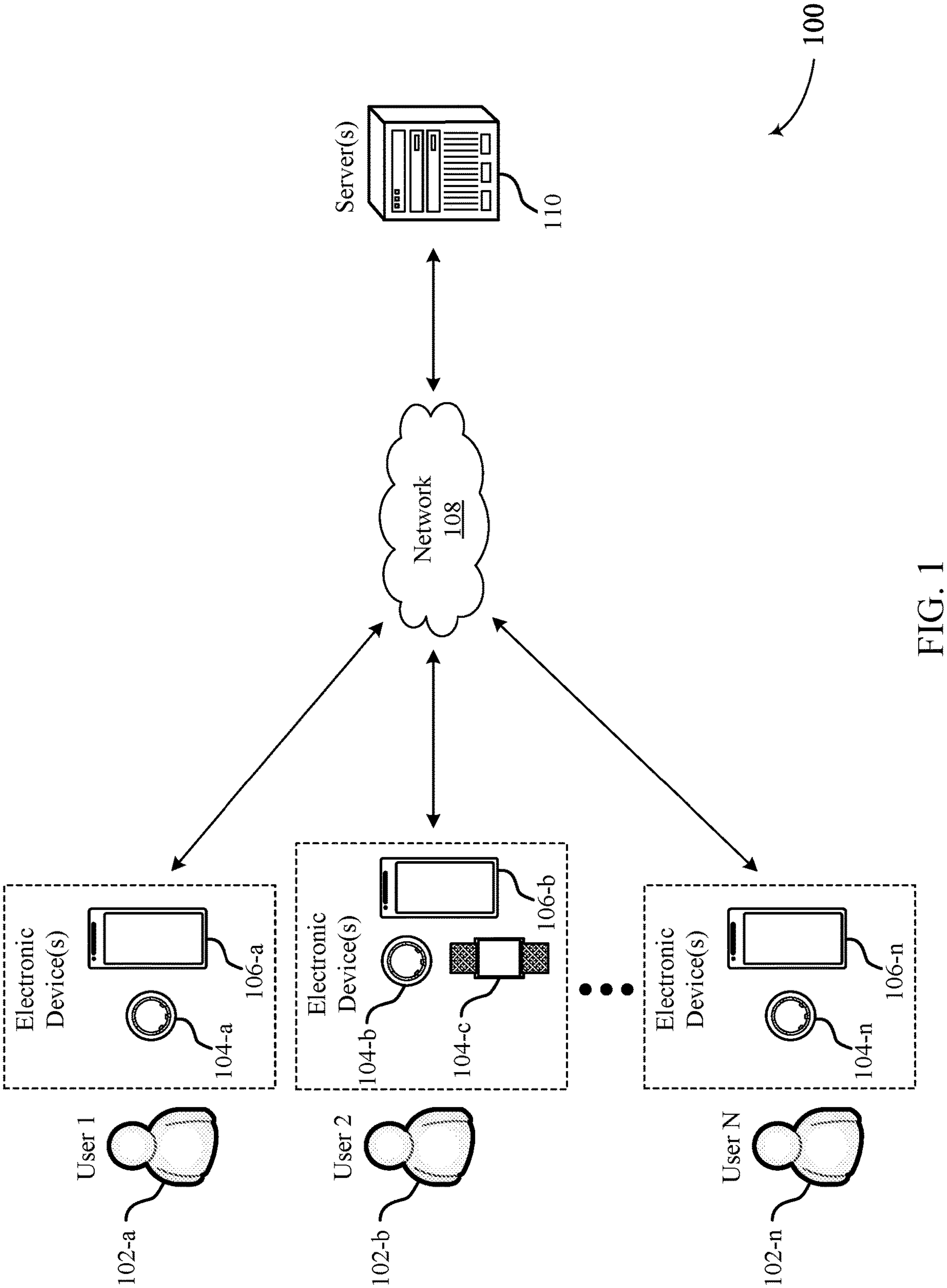
FIG. 1 illustrates an example of a system that supports the detection of snoring and environmental sounds in accordance with aspects of the present disclosure.

Wearable devices may be configured to collect physiological data from users, such as heart rate data, heart rate variability (HRV) data, movement data, and other information about the user. In some examples, there may be a correlation between the physiological data of a user and their sleep quality. In particular, the physiological data collected by a wearable device while the user sleeps may be used to determine a relative sleep quality of the user. However, the physiological data alone may not provide enough information regarding factors that may be affecting sleep restfulness. For example, other factors that may affect a user's sleep may include characteristics of the user's surroundings while sleeping, such as temperature, light, humidity, and sound while the user sleeps. As such, physiological data alone may not provide the entire picture regarding factors that are negatively (or positively) affecting sleep quality of a user.

In accordance with examples as described herein, a sleep quality of a user may be evaluated by combining physiological data collected via a wearable device, along with environmental sound data collected via one or more external devices. For example, a microphone on a device (e.g., a device or phone of the user, a charging station for the wearable device, or the wearable device itself) may monitor for environmental sounds while a user sleeps, which may help provide a more complete picture regarding factors that may affect the user's sleep quality. In some examples, sleep sounds may be used to improve sleep stage classification (e.g., determine when the user is transitioning between deep, light, and rapid eye-movement (REM) sleep stages, for example, based on sounds detected by the charger device). Additionally, or alternatively, a device may monitor nocturnal sound data as the user sleeps and may detect and identify specific sound instances (e.g., the user getting up or moving, a baby crying, road noise, or other sounds). In some examples, sound data may be combined with other data, such as physiological data, to determine relationships between the sleep sound data and sleep quality. For instance, a correlation between a user's sleep quality and nocturnal sounds, such as sounds from pets, children, cars, snoring, or other sounds, may be identified and presented to the user via an application.

In some cases, physiological data may be used to identify and label sounds. For example, a drop (e.g., a decrease) in recorded blood oxygen saturation (e.g., SpO2) values may be used to determine that a sound instance corresponds to a user snoring (and/or diagnose sleep apnea). Additionally, or alternatively, a machine learning model trained on sound samples may be used to identify detected sound instances. The user may be presented with a graphic identifying sounds that occurred during their sleep period, and how these sounds correlate to their sleep quality throughout the night. In some cases, the user may be able to listen to and re-label the sounds to ensure accuracy. Accordingly, a user may receive information associated with how nocturnal noises affect their sleep, which may improve a user's ability to improve their sleep quality.

Aspects of the disclosure are initially described in the context of systems supporting physiological data collection from users via wearable devices. Aspects of the disclosure are additionally illustrated in the context of graphical user interfaces (GUIs) that support techniques related to the detection of snoring and environmental sounds. Aspects of the disclosure are further illustrated by and described with reference to apparatus diagrams, system diagrams, and flowcharts that relate to detection of snoring and environmental sounds.

FIG. 1 illustrates an example of a system 100 that supports the detection of snoring and environmental sounds in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, HRV, actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a*associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b* , where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a REM sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state: 2) circadian rhythms: 3) non-endogenous daily rhythms shown to be imposed on top of circadian rhythms, as in work schedules: 4) weekly rhythms, or other artificial time periodicities exogenously imposed (e.g. in a hypothetical culture with 12 day "weeks," 12 day rhythms could be used): 5) multi-day ovarian rhythms in women and spermatogenesis rhythms in men: 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for evaluating a sleep quality of a user 102 by combining sound data collected via a microphone of a wearable device 104, a user device 106, a charger device of the wearable device 104, or another device, with physiological data collected by the wearable device 104. In some examples, the sound data and the physiological data may be transmitted (e.g., by the user device 106 or the wearable device 104) to the servers 110 via the network 108. In some cases, to maintain sound data, which may include sensitive or private user recordings, the user device 106 may transmit an indication of the sound data to the servers 110 that may not include the actual recordings of the sound data (e.g., the wearable device 106 may extract "features" from the sound data/recording, and may transmit the sound "features" to the server rather than the actual sound data/recording to improve user 102 privacy).

In some examples, the sound data may be combined with the physiological data to improve sleep stage classification over a sleep duration of the user 102. For example, sound data and physiological data may be used to determine whether a user 102 is in deep sleep, light sleep, an awake sleep stage, or REM sleep based on, for example, an amount of movement of the user (where the movement may be identified via acquired sound data). In some examples, the servers 110 or a device, such as the user device 106 or the wearable device 104, may determine sound instances within the sound data and may determine labels for each sound instance. For example, a spectrogram (e.g., a Mel-spectrogram) may be generated for each sound instance and compared to a set of sample spectrograms to determine a label for each sound instance (e.g., to classify each sound instance). Additionally, or alternatively, the physiological data, such as movement data or oxygen saturation values, may be used to classify the sound instances. The user 102 may be presented with information associated with how nocturnal noises affect their sleep via an application of the user device 106, which may improve a user's ability to improve their sleep quality.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
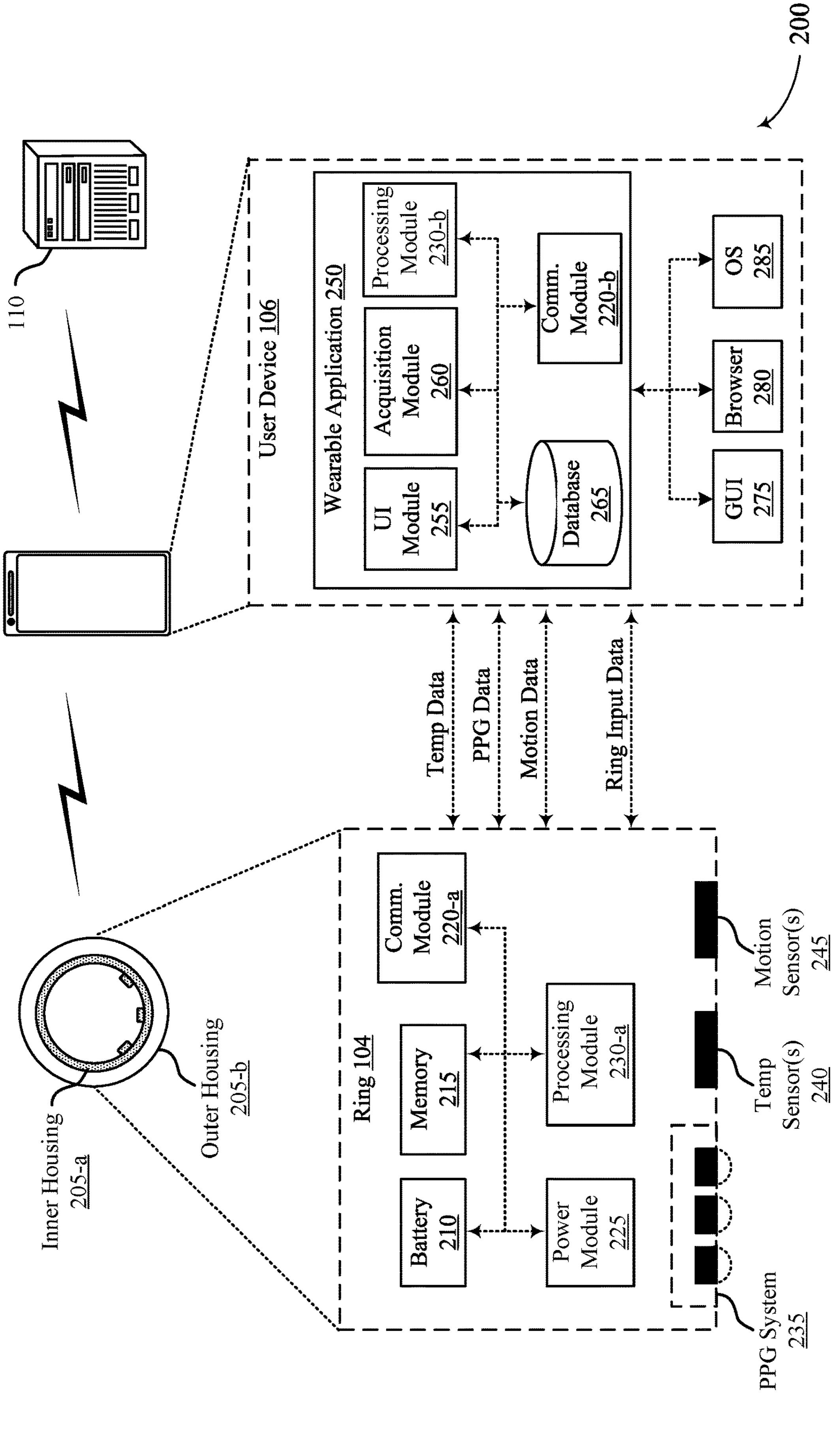
FIG. 2 illustrates an example of a system that supports the detection of snoring and environmental sounds in accordance with aspects of the present disclosure.

FIG. 2 illustrates an example of a system 200 that supports the detection of snoring and environmental sounds in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen saturation levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate (s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-b can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for evaluating a sleep quality of a user based on sound data and physiological data. For instance, a device (e.g., a user device 106, a ring 104, or another external device) may record sound data via a microphone to monitor for environmental sounds while a user sleeps. In some examples, the sound data and physiological data collected using the ring 104 may be used to evaluate a sleep quality of the user. For example, the sound data and the physiological data may be used to improve sleep stage classification (e.g., identify when the user is transitioning between sleep stages, a quantity of time spent in each sleep stage). Additionally, or alternatively, the sound data may be classified into sound instances, which may be presented to the user using an application of the user device 106 such that the user may be aware of sounds that may affect the sleep quality of the user. Accordingly, by using sound data and physiological data to provide information about a user's sleep quality, the user may take steps to improve their sleep quality.

In some examples, the sound data and the physiological data may be communicated (e.g., by a user device 106) to the servers 110. The servers 110 may analyze the sound data, the physiological data, or both, and may combine the sound data and the physiological data to determine an indication of the user's sleep quality, which may be transmitted to the user device 106 for display to the user within an application (e.g., via a GUI). In some cases, the sound data communicated to the servers 110 may include volume, classification (e.g., cause/type of the sound instance), or both, included with sound instances within the sound data. For example, the user device 106 may classify the sound instances, and may assign labels to each sound instance. The user device 106 may then transmit an indication of a volume and a label associated with each sound instance, such that the actual sound recordings may not be reconstructed, thereby enhancing the privacy of the user.

Figure 3:
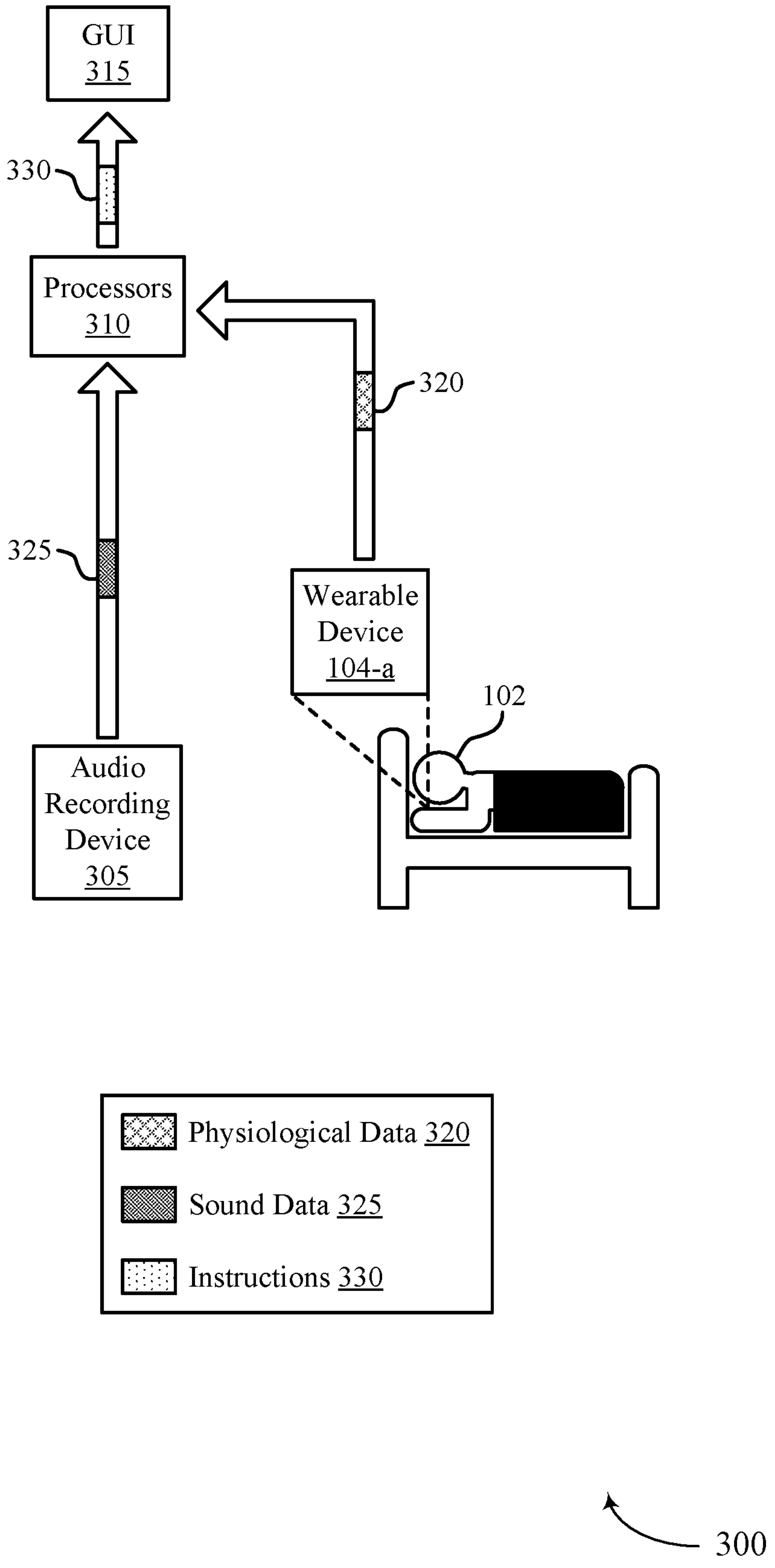
FIG. 3 shows an example of a system that supports the detection of snoring and environmental sounds in accordance with aspects of the present disclosure.

FIG. 3 shows an example of a system 300 that supports the detection of snoring and environmental sounds in accordance with aspects of the present disclosure. The system 300 may implement, or be implemented by, the system 100, the system 200, or both. For example, the system 300 includes a wearable device 104-*a*, which may be an example of a wearable device 104 as illustrated herein, with reference to FIGS. 1 and 2.

The wearable device 104-*a* may be configured to collect physiological data 320 from a user 102. For example, the wearable device 104-*a* may collect movement data, heart rate data (e.g., heart rate, HRV), blood oxygen saturation (e.g., SpO2) data, and other information about the user 102. In some examples, the physiological data 320 may be used to determine a sleep quality (e.g., a sleep quality metric) associated with the user 102, which may be presented to the user 102 via an application of a user device 106 of the user 102. In some cases, however, the physiological data 320 alone may not provide sufficient information regarding factors that may affect the sleep quality of the user 102. For instance, the wearable device 104-*a* may be unable to collect information regarding the surroundings of the user 102, which may provide additional insight into the sleep quality of the user 102.

In accordance with examples as described herein, the system 300 may include one or more audio recording devices 305 (e.g., audio recording components). An audio recording device 305 may include a microphone and may be configured to collect sound data 325 during a sleep interval of the user 102 by being placed near the user 102 (e.g., in a same room) during the sleep interval. In some examples, the audio recording device 305 may be a user device 106 of the user 102, a charging device (e.g., base) configured to charge the wearable device 104-*a* when mounted on the charging device, the wearable device 104-*a* itself, a third-party device, a smart speaker, a home automation device, a security system, or another device. Accordingly, the audio recording device 305 may be used to collect the sound data 325 while the user 102 sleeps.

In some examples, multiple audio recording devices 305 may be used to collect sound data 325. For example, a charger device and a user device 106 may both record audio during the sleep interval. By using multiple audio recording devices 305, multiple recordings may be analyzed (e.g., by processors 310) to determine a location for sounds occurring during the sleep instance. For example, the user 102 may input a location of each audio recording device 305 within an environment of the user 102 (e.g., a room), which may allow for a mapping of locations of sounds occurring during the sleep instance on the environment. The mapping may be presented to the user 102 through an application of the user device (e.g., via a GUI 315). For instance, separate audio recording devices 305 may be placed on each side of the user's bed. In some cases, the use of multiple audio recording devices 305 may improve the ability of the system to identify the cause/source of sound instances within the sound data 325, such as differentiating whether sound instances are caused by one of multiple people or pets sleeping in the same room.

A start of the sleep interval may be based on a time at which the user 102 falls asleep (e.g., when the physiological data 320 indicates that the user has fallen asleep), and/or when the audio recording device 305 begins recording. In some examples, the audio recording device 305 may begin recording based on an input by the user 102. For example, the user 102 may initiate the recording (e.g., manually) through an application of the user device 106. Additionally, or alternatively, the audio recording device 305 may be configured to automatically begin recording when the user 102 sleeps or has fallen asleep. For instance, the wearable device 104-*a* may detect that the user 102 has fallen asleep based on the physiological data 320, and the wearable device 104-*a* may signal the audio recording device 305 to begin recording (e.g., directly or via the user device 106).

Similarly, the audio recording device 305 may cease recording, which may be associated with an end of the sleep interval, based on an input by the user 102 (e.g., based on the user opening the wearable application 250) or automatically by detecting that the user 102 is awake or has awakened (e.g., based on the sound data 325 or an indication by the wearable device 104-*a*). For example, the processors 310 may determine that the user 102 has awakened if the sound data 325 or the physiological data 320 indicate that the user 102 is moving (e.g., above a threshold amount) or speaking. Additionally, or alternatively, the processors 310 may determine that the user 102 has awakened based on a heart rate of the user or a temperature of the user (e.g., from the physiological data 320). As such, the processors 310 may transmit an instruction to the audio recording device 305 to instruct the audio recording device 305 to terminate acquisition of the sound data 325 (e.g., cease recording of the environment).

In additional or alternative implementations, the audio recording device 305 may selectively start/stop recording based on identified sounds. For example, in some cases, the audio recording device 305 may selectively start recording when a sound level exceeds a certain threshold, and may stop recording when the sound level drops below the same (or different) threshold. In this example, the audio recording device 305 may be "voice/sound activated" in that it does not record continuously, but rather records only when there are sounds that may be valuable to the system 300 for performing techniques described herein. Similarly, in some cases, the user may be able to select or define which types of noise instances that the audio recording device 305 is to record. For example, the user may indicate for the audio recording device 305 to record only noise instances that satisfy (e.g., above or below) a defined volume threshold, a duration threshold, a frequency threshold, or a combination thereof, or record only noise instances associated with a particular type or source (e.g., record talking and snoring noise instances, but not other types of noise instances such as a clock ticking or car noises from the street). Moreover, in similar cases, the audio recording device 305 may be configured to record all types of noise instances, but may be configured to store or save only those noise instances that satisfy the user-defined criteria (and discard noise instances that do not satisfy the criteria).

In some examples, the wearable device 104-*a* may output the physiological data 320 to processors 310. Similarly, the audio recording device 305 may output the sound data 325 to the processors 310. In some examples, the processors 310 may be part of servers 110, as described herein with reference to FIGS. 1 and 2. Additionally, or alternatively, the processors 310 may be part of a user device 106 of the user 102, the audio recording device 305, the wearable device 104-*a*, or another device. In other words, processing and other functions described herein as being carried out at the processors 310 may be carried out by processors within the user device 106, the wearable device 104-*a*, the audio recording device 305, or any combination thereof.

The processors 310 may evaluate the sleep quality of the user 102 based on the sound data 325 and the physiological data 320, and the processors 310 may determine one or more sleep quality metrics for the user 102. Additionally, or alternatively, the processors 310 may determine one or more sleep stages that the user 102 may experience during the sleep interval, transitions between the sleep stages, a duration of each sleep stage, or a combination thereof, based on the sound data 325 and the physiological data 320. In some examples, the processors 310 may determine one or more sound instances within the sound data 325, and the processors 310 may determine one or more labels to classify each sound instance. Techniques related to these uses of the sound data 325 and the physiological data 320 by the processors 310 are described in further detail herein, with reference to FIG. 4.

In some cases, the sound data 325 output by the audio recording device 305 may not include an actual recording collected by the audio recording device 305. In other words, in some cases, the audio recording device 305 may partially "scrub" the sound data 325 that is transmitted to the processors 310 in order to improve user privacy. In particular, the system may be configured to classify and filter out sensitive portions of the sound data 325, such as portions of the sound data 325 that have been identified as speech or sexual activity. In such cases, the system 300 may be configured to indicate or show such "scrubbed" periods as "not recorded," or may drop such portions from the sound data 325 altogether.

For example, the sound data 325 may include an indication of the actual recording, such as an indication of sound instances occurring during the recording, or "features" extracted from the sound recording. The indication may include a volume of each sound instance and a label of each sound instance, for example. In some cases, the sound data 325 may include numerical or graphical representations of sound instances which may be used to perform analysis (e.g., classification of the sound instances) by the processors 310. For instance, the sound data 325 may include numerical values corresponding to sound instances which may be used by a machine learning model of the processors 310, a spectrogram (e.g., a Mel-spectrogram) corresponding to sound instances, or both, but the sound data 325 may not include sufficient information to reproduce the actual recording. As such, the privacy of the user 102 may be enhanced, as the actual recordings performed by the audio recording device 305 may remain within a device of the user 102 without being transmitted to external devices or servers. Additionally, or alternatively, the sound data 325 may be encrypted, such that a third party that may intercept a transmission of the sound data 325 may not be able to reproduce the recording by the audio recording device 305.

The processors 310 may output instruction 330 to a GUI 315 to cause the GUI 315 to display an indication of the one or more sleep quality metrics, the one or more sleep stages, transitions between the sleep stages, the sound instances during the sleep interval, or any combination thereof. In some examples, the GUI 315 may be included within a user device 102 of the user 102. The GUI 315 may display the sound instances recorded by the audio recording device 305 on a timeline, and the GUI 315 may allow the user 102 to initiate playback of an audio recording associated with each sound instance. Aspects of the GUI 315 are described in more detail herein, with reference to FIG. 5.

In some examples, the instruction 330 may determine to include or exclude an indication of a sound instance based on previous responses from the user 102. For example, the processors 310 may determine that some sounds (e.g., sounds below a volume threshold, sounds above a frequency threshold) do not appear to affect the user 102 (e.g., based on previous movement data, sleep stage data, the sleep quality metrics), which may indicate that the user 102 may be a heavy sleeper, and the processors 310 may exclude these sounds from the instruction 330 for display by the GUI 315. Additionally, or alternatively, if the processors 310 determine that some sounds (e.g., based on a volume threshold or a frequency threshold) do appear to affect the user 102 (e.g., based on previous movement data, sleep stage data, the sleep quality metrics), which may indicate that the user 102 may be a light sleeper, the processors 310 may include these sounds from the instruction 330 for display by the GUI 315. Stated differently, the system may "learn" which sounds to include or exclude for processing and/or displaying to the user by determining what type of sleeper the user is (e.g., heavy sleeper, light sleeper) and/or what types of sounds appear to affect the user's sleep.

In additional or alternative implementations, the system 300 may include one or more devices configured to capture video data associated with time intervals that the user is sleeping. For example, the audio recording device 305, the user device 106, and/or a dedicated video recording device may be configured to acquire video data in addition to the audio data collected by the audio recording device 305. In some cases, acquired video data may provide additional information and context that may be used to improve sleep quality evaluation (e.g., improve sleep staging). For example, video data may be used to more accurately or reliably detect a source of snoring (e.g., whether it is the user snoring, or their spouse), validate a source of sounds (e.g., video data may confirm that noise instances are due to a user getting out of bed or rolling over in the middle of the night). Further, as described previously with respect to audio data, video recording may be automated so the video recording device only records when certain criteria are met (e.g., only record specific movements, only record when certain sounds are detected, only record movement on one side of the bed/room, record only when the subject is larger than some threshold (record users, but not dogs/cats), and the like). Further, as described previously herein with respect to audio data, the system 300 may be configured to "scrub" and/or refrain from video recording (or saving) certain types of activities (e.g., record when the user gets out of bed, but don't record movements that take place within the bed, such as sexual activities).

Figure 4:
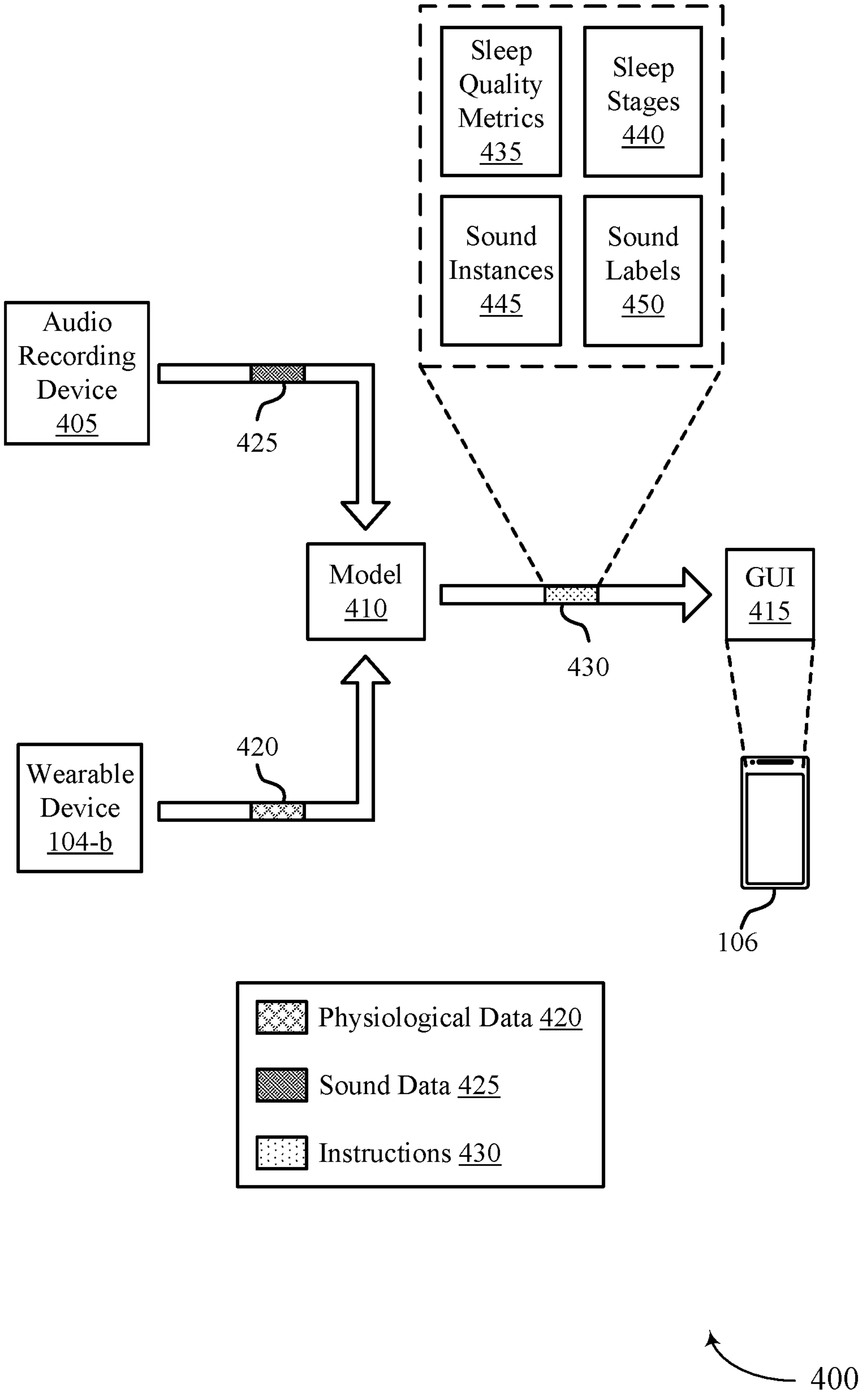
FIG. 4 shows an example of a system that supports the detection of snoring and environmental sounds in accordance with aspects of the present disclosure.

FIG. 4 shows an example of a system 400 that supports the detection of snoring and environmental sounds in accordance with aspects of the present disclosure. The system 400 may implement, or be implemented by, the system 100, the system 200, the system 300, or any combination thereof. For example, the system 400 includes an audio recording device 405, a wearable device 104-*b*, a GUI 415, and a user device 106, which may be examples of corresponding devices as described herein, with reference to FIGS. 1 through 3.

In accordance with examples as described herein, the audio recording device 405 may transmit an indication of sound data 425 to be used by a model 410 (e.g., a machine learning model, an algorithm, a process, or any combination thereof). Similarly, the wearable device 104-*b* may transmit an indication of physiological data 420 to be used by the model 410. In some examples, the model 410 may be implemented within processors 310, as described herein with reference to FIG. 3. For instance, the model 410 may be implemented at a server 110, as described herein with reference to FIGS. 1 and 2. In some of these examples, the physiological data 420 and the sound data 425 may be obtained by the user device 106 (e.g., from the wearable device 104-*b* and the audio recording device 405, respectively), and the user device 106 may output the physiological data 420 and the sound data 425 to the servers 110 for use with the model 410. Alternatively, the model 410 may be implemented within any of the user device 106, the wearable device 106-*b*, the audio recording device 405, or another device.

In some examples, the model 410 may be used (e.g., by one or more processors) to determine one or more sleep quality metrics 435 associated with a sleep quality of a user throughout a sleep interval. For example, the sleep quality metrics 435 may be based on the sound data 425, the physiological data 420, or a combination thereof. In some examples, the sleep quality metrics 435 may include one or more values that indicate a restfulness of the user, which may be based on the duration of the sleep interval, a quantity of sound instances 445 in the sound data 425, a volume of the sound instances 445 (e.g., a cumulative volume, a maximum volume), an amount of movement by the user during the sleep interval (e.g., determined based on the sound data 425 and the physiological data 420), or other measures associated with the sleep quality of the user during the sleep interval. In some cases, the one or more sleep quality metrics may be or include a Sleep Score, as described herein with reference to FIG. 1.

In some examples, the model 410 may be used to identify one or more sleep stages 440 occurring during the sleep interval. For example, the model 410 may identify transitions between sleep stages of the user during the sleep interval, which may include classifying the physiological data 420 into one or more sleep stages (e.g., a deep sleep stage, a light sleep stage, a REM sleep stage, an awake stage).

In some examples, the sleep stages may be identified based on the sound data 425. In particular, it has been found that users exhibit varying levels of movement and snoring while in different sleep stages, and when transitioning between different sleep stages. As such, the sound data 425 (which may include sound instances associated with the user moving, snoring, etc.) may be used to more accurately identify what sleep stage the user is in, and more accurately identify when the user is transitioning between sleep stages. For instance, a breathing volume may be used to identify a sleep stage, and heavier breathing may indicate that the user is in deep sleep or in REM sleep, while lighter breathing may indicate that the user is in light sleep or awake. Additionally, or alternatively, a quantity of sound instances may be used to determine a sleep stage. For example, a lower quantity of sound instances may be associated with less movement by the user, which may indicate that the user is in REM sleep or deep sleep.

In some examples, the sleep quality metrics 435 may be based on the sleep stages 440. For instance, the sleep quality metrics 435 may be based on the duration of one or more sleep stages 440. In some examples, the model 410 may calculate a duration that the user spent in each of the sleep stages 440 and may evaluate the sleep quality metrics 435 based on the durations and, for example, one or more thresholds. In some cases, a higher sleep quality metric 435 (e.g., Sleep Score) may be based on a higher duration of a sleep stage 440, such as a deep sleep stage or a REM sleep stage, during the sleep interval, or a higher proportion of the sleep stage 440 relative to other sleep stages 440.

In some examples, the model 410 may be used (e.g., by one or more processors) to identify one or more sound instances 445 within the sound data occurring throughout the sleep interval of the user. For example, isolated sound recordings may be assigned to a single sound instance 445, and the isolated sound recording may correspond to one or more spikes in volume relative to a background (e.g., base) volume. In some examples, the model 410 may use a threshold volume (e.g., minimum volume) to classify sound instances 445 within the sound data 425, and the threshold volume may be modified by the user to adjust the sensitivity of the model 410, which may affect the quantity of sound instances 445 identified within the sound data 425.

The model 410 may classify the one or more sound instances 445 with one or more sound labels 450 based on the sound data 425 and the physiological data 420. For example, the model 410 may determine a change in one or more metrics of the physiological data 420 and assign a sound label 450 to a sound instance 445 based on the change. In some examples, the model 410 may assign a "snoring" label to a sound instance 445 based on determining a drop (e.g., decrease) in a blood oxygen saturation level (e.g., SpO2) in the physiological data 420 that occurs during a time duration associated with (e.g., occurring prior to, during, relatively close to) the sound instance 445. Similarly, the model 410 may determine a change in a metric (e.g., gyroscope or accelerometer data) of the physiological data 420 that indicates movement of the user and may assign a movement label to a corresponding sound instance 445 (e.g., a sound instance 445 occurring during a time duration associated with the movement).

In some examples, the model 410 may compare sound instances 445 with a set of sample sound recordings (e.g., a sound bank) to classify the sound instances 445 with sound labels 450 (e.g., using a machine learning model). In some cases, the set of sample sound recordings may be aggregated from the Internet, from other users 102 (e.g., from recordings from other users 102, from input from the other users 102), and/or manually uploaded by the user 102 (e.g., the user 102 may initiate a "training" session where the user sets off their alarm clock to generate an "alarm clock" sample sound recording for future comparison). For example, the model 410 may identify that a sound instance 445 matches a sample sound recording of the set of sample sound recordings, and the model 410 may assign a corresponding sound label 450 to the sound instance 445. In some cases, the model 410 may determine a confidence value associated with the match (e.g., a closest match) between a sound instance 445 and a sample sound recording, and the model 410 may assign the corresponding sound label 450 if the confidence value is above a threshold value. If the confidence value is below the threshold value, the model 410 may assign an unclassified label to the sound instance 445. The sound labels 450 may include any of a snoring label, a coughing label, a breathing label, a talking label, a pet label, a children label, a movement label, a footsteps label, a sneezing label, an alarm clock label, a thunderstorm label, a laughing label, a rain label, an unclassified label, or another label, and the set of sample sound recordings may include examples corresponding to any of these labels.

In some cases, the model 410 may classify the sound instances 445 using a set of spectrograms (e.g., a spectrogram bank) associated with a set of sample sounds (e.g., a sound bank) that may correspond to the sound labels 450. For example, the model 410 may calculate a spectrogram (e.g., a Mel-spectrogram) for each sound instance 445, or the model 410 may obtain one or more spectrograms indicated in the sound data 425. The model 410 may compare the spectrogram for each sound instance 445 with the set of spectrograms, and the model 410 may assign a corresponding label based on a sample sound with a closest match. In some examples, a match between a sound instance 445 and a sample sound associated with a sample spectrogram may be associated with a confidence value, and if the confidence value is below a threshold, the model 410 may assign an unclassified label to the sound instance 445.

In some cases, such as when the sound data 425 does not include the actual recordings of the sound instances 445, the sound data 425 may include information that may allow the model 410 to classify the sound instances 445. For example, the sound data 425 may include a set of numerical values associated with the recordings (e.g., the sound data 425 may be converted to a series of "1s" and "0s"), which may allow the model 410 to identify the sound instances 445, assign sound labels 450 to the sound instances 445, or both. In some cases, the sound data 425 may include a set of numerical values for each sound instance 445, which may be used by the model 410 for a machine learning model to obtain the sound labels 450 (e.g., using a set of sample numerical values associated with a respective set of sample sounds). Additionally, or alternatively, the sound data 425 may include one or more spectrograms (e.g., Mel-spectrograms) which may be used by the model 410 to identify the sound instances 445, assign sound labels 450 to the sound instances, or both, based on the set of sample spectrograms.

In some examples, the model 410 may identify a person associated with a sound instance 445, such as a snoring sound instance 445 or a movement sound instance 445. For example, the model 410 may identify a first fundamental frequency associated with sound instances 445, such as snoring sound instances 445, corresponding to a first person (e.g., the user). Additionally, the model 410 may identify a second fundamental frequency associated with sound instances 445 corresponding to a second person (e.g., a partner of the user, another person). The model 410 may then identify that a subsequent sound instance 445 is associated with the first person or the first person by comparing a frequency of the subsequent sound instance 445 with the first fundamental frequency and the second fundamental frequency. In some examples, the model 410 may use a machine learning model to determine the first fundamental frequency and the second fundamental frequency, and the machine learning model may be trained with prior sound data 425 or inputs from the user (e.g., for which snoring instance corresponds to which person). Accordingly, the user may be notified (e.g., via the GUI 415) of a person that may correspond to a sound instance 445, which may aid the user in identifying which person is the source of snoring, movement, or other sounds.

In some cases, the model 410 may identify patterns of the sleep quality of the user based on the sound data 425 and the physiological data 420. For example, the model 410 may determine that a sleep quality of the user is decreased (e.g., based on the physiological data 420, on a quantity of movement of the user) on nights on which the sound data 425 indicates snoring instances have occurred, and the model 410 may reflect the decreased sleep quality on a Sleep Score which may be presented to the user (e.g., via the GUI 415). In some cases, the model 410 may output instructions 430 that may suggest to the user to be diagnosed for sleep apnea based on the detection of one or more snoring instances.

In some examples, the model 410 may identify reasons for a decrease in sleep quality. For instance, the model 410 may determine that a decrease in sleep quality, a decrease in a duration of sleep, or a decrease in a duration of a sleep stage (e.g., deep sleep) during the sleep interval is caused by factors in the sound data 425 and the physiological data 420 (e.g., an emergency siren may interrupt sleep, a room temperature is too high). In some other examples, the model 410 may obtain weather information (e.g., from a user device, an audio recording device, a server) which may provide information which may affect sleep quality, such as storms, wind, snow (e.g., snowplows), rain, temperature, or other factors. Additionally, or alternatively, these factors that may affect sleep quality may be used by the model 410 to identify sound instances within the sound data 425 (e.g., snowplows due to snow on the forecast, rain sounds, thunder sounds, or other sounds). The model 410 may provide a suggestion for the reasons that may be affecting quality to the user (e.g., via the GUI 415).

The model 410 may output instructions 430 to the GUI 415 of the user device 106. The instructions 430 may cause the GUI 415 to display any of the sleep quality metrics 435, the sleep stages 440, the sound instances 445, and the sound labels 450. Examples of displays by the GUI 415 are illustrated with more detail herein, with reference to FIGS. 5A and 5B. Accordingly, by using the sound data 425 and the physiological data 420 to provide information about a user's sleep quality, the user may be more informed about their sleep quality, which may lead to improved sleep quality.

Figure 5B:
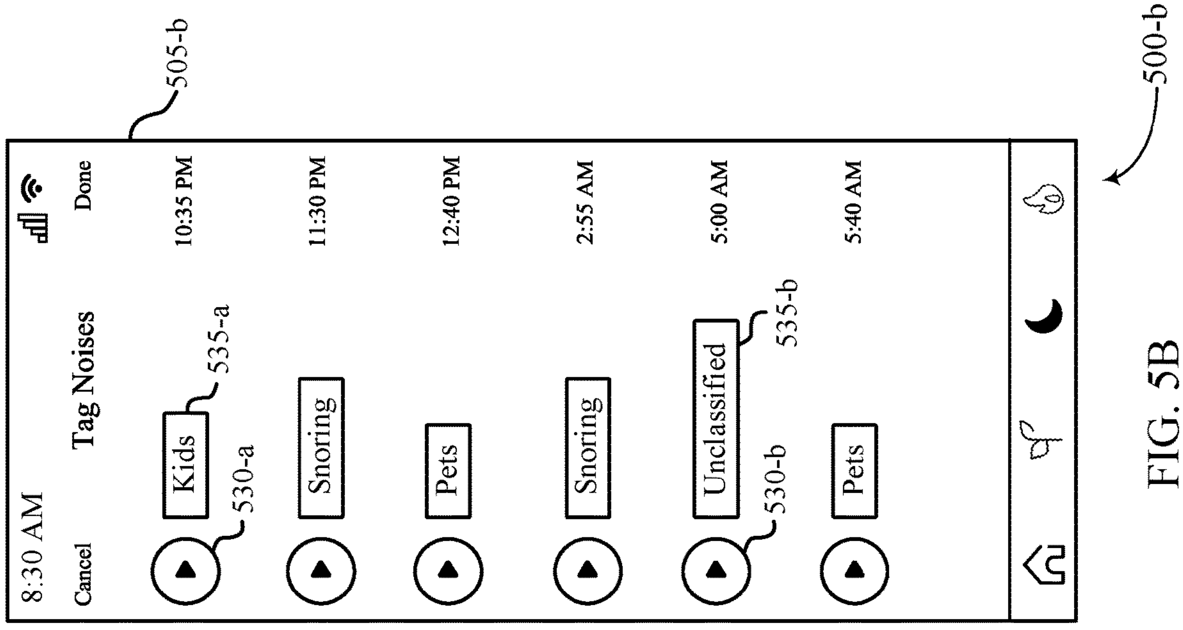
FIGS. 5A and 5B show examples of graphical user interfaces (GUIs) that support detection of snoring and environmental sounds in accordance with aspects of the present disclosure.
Figure 5A:
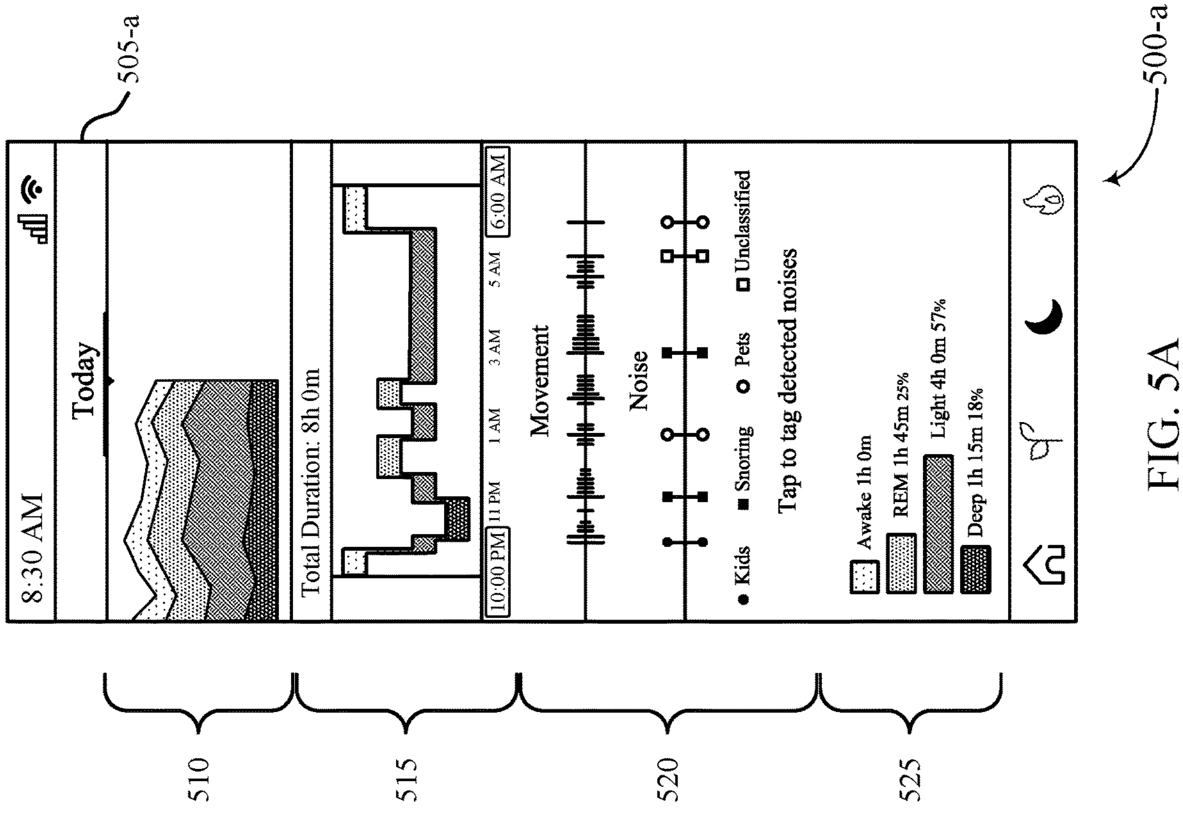

FIGS. 5A and 5B show examples of a GUI 500-*a* and a GUI 500-*b* that support the detection of snoring and environmental sounds in accordance with aspects of the present disclosure. The GUI 500-*a* and GUI 500-*b* may be displayed on a screen 505-*a*, 505-*b* of a user device 106 via an application, as described herein, based on instructions received from one or more processors (e.g., of a server 110, the user device 106, a wearable device 104, an audio recording device, or another device).

The GUI 500-*a* may display information that may be obtained based on sound data collected by an audio recording device and physiological data collected by a wearable device 104, as described herein. For example, the GUI 500-*a* may display information related to sleep quality metrics, sleep stages, sound instances, and sound labels. In some examples, the GUI 500-*a* may display the information in a different order than illustrated in FIG. 5A, and some information may be added or omitted from the GUI 500-*a* .

At section 510, the GUI 500-*a* may display an indication of a duration of each sleep stage of a set of sleep stages. For example, the GUI 500-*a* may illustrate a graph that illustrates a total duration that a user has spent in each sleep stage of the set of sleep stages. In some cases, each sleep stage may be identified based on a different color or pattern (e.g., as defined in the section 525), which may be used throughout the GUI 500-*a*. FIG. 5A illustrates an example corresponding to four sleep stages, which may be an awake stage, a REM sleep stage, a light sleep stage, and a deep sleep stage, though examples with more sleep stages or fewer sleep stages are possible. In some examples, the user may be able to scroll on the graph on section 510, and the GUI 500-*a* may display information for previous sleep intervals of past days. As such, the user may compare the time spent in each sleep stage across different days. In some cases, scrolling to a past day may update the information displayed in other sections of the GUI 500-*a* to information corresponding to the past day.

At section 515, the GUI 500-*a* may display a total duration for the sleep interval (e.g., in hours and minutes). The GUI 500-*a* may also display transitions between the sleep stages. For example, the section 515 may include a timeline that displays which sleep stage the user was experiencing during portions of the sleep interval. The timeline may also include one or more time labels, which may include a start of the sleep interval and an end of the sleep interval (e.g., which may be set by the user), one or more times in between the start and end, or a combination thereof. As such, the user may be aware of which sleep stage (e.g., awake stage, REM stage, light sleep stage, deep sleep stage) the user experienced during which time intervals over the sleep interval.

At section 520, the GUI 500-*a* may include a movement timeline that displays movements determined based on the sound data, the physiological data, or both. For example, the section 520 may include a timeline with one or more movement instances that may mark a time at which a corresponding movement occurred. In some examples, a size of each movement instance (e.g., a line, a tick) may be based on the amount of movement. For instance, a movement with a long duration, high intensity, associated with a sound with a high volume, or a combination thereof, may be associated with a relatively larger movement instance. Meanwhile, a movement with a short duration, short intensity, associated with a sound with a low volume, or a combination thereof, may be associated with a relatively shorter movement instance.

The section 520 may also include a noise timeline that displays sound instances determined based on the sound data, the physiological data, or both. Similarly to the movement instances, the sound instances may be displayed on a timeline based on a time at which the sound instance occurred. In some examples, each noise instance may include an indication of a corresponding label. For example, each noise instance on the noise timeline may have a display color that corresponds to a label, and the label and corresponding color may be listed below the noise timeline. Additionally, or alternatively, a different indication may be used, such as a pattern or shape. In some examples, each sound instance on the sound timeline may vary in size depending on a relative volume of the sound instance (e.g., average volume) relative to a background (e.g., base) volume or relative to other sound instances.

The section 520 may allow the user to listen to the sound instances and relabel sound instances. For example, the user may tap on text that may read "Tap to tag detected noises," or on the noise timeline itself, and the GUI 500-*b* may be displayed, which may allow the user to listen to and relabel sound instances. This is described in more detail herein, with reference to the GUI 500-*b*.

At section 525, the GUI 500-*a* may display a graph that illustrates a total duration that a user has spent on each sleep stage of the set of sleep stages. The section 525 may include a label for each sleep stage (e.g., "Awake," "REM," "Light," "Deep"), and may indicate a corresponding color for each sleep stage. The corresponding colors may be used to identify each sleep stage throughout the GUI 500-*a*, such as in the section 510, the section 515, and the section 525. The section 525 may include a total duration that the user spent in each sleep stage throughout the sleep interval (e.g., in hours and minutes). Additionally, or alternatively, the section 525 may include a proportion of time that the user spent in each sleep stage, such as by displaying a percentage associated with the proportion of each sleep stage in relation to the duration of the sleep interval.

The GUI 500-*b* may display a list of sound instances based on the sound data, and the GUI 500-*b* may allow a user to initiate playback of each sound instance and label or relabel sound instances. For example, the user may tap on a button 530-*a* to initiate playback of a sound instance, which may have been labeled as a kids sound instance. The user may tap on the kids label 535-*a*, which may prompt the user with a relabeling prompt that may allow the user to input a different label for the sound instance, for example, if the original label is incorrect. As such, the user may replace a sound label 535 of a sound instance with an updated label 535.

The GUI 500-*b* may include a time corresponding to a time at which each sound instance occurred, and the time may match a time shown in the sound timeline of the section 520. In some examples, the GUI 500-*b* may include a button to remove sound instances. In some cases, the button to remove instances may appear after tapping on a label 535 (e.g., on a relabeling prompt). In some examples, the user may tap a button that may be labeled "Done," which may save changes to the list of sound instances and corresponding labels. In some other examples, the user may tap a button that may be labeled "Cancel," which may return to a previous screen (e.g., the GUI 500-*a*) without saving changes made by the user to the list of sound instances and corresponding labels.

In some cases, as described herein, a model or process for identifying the sound instances may not be able to recognize a sound instance (e.g., from a set of sample sounds) and may assign an unclassified label 535-*b* to a sound instance. As such, the user may tap on a button 530-*b* to initiate playback of the unrecognized sound instance, which may allow the user to identify what the sound instance corresponds to. Additionally, or alternatively, the user may tap on the unclassified label 535-*b*, which may prompt the user to enter text for replacing the unclassified label 535-*b* with an updated label 535.

Accordingly, by implementing aspects of the GUI 500-*a* and the GUI 500-*b*, the user may be informed of various aspects of their sleep quality, which may support the user in improving their sleep quality.

Figure 6:
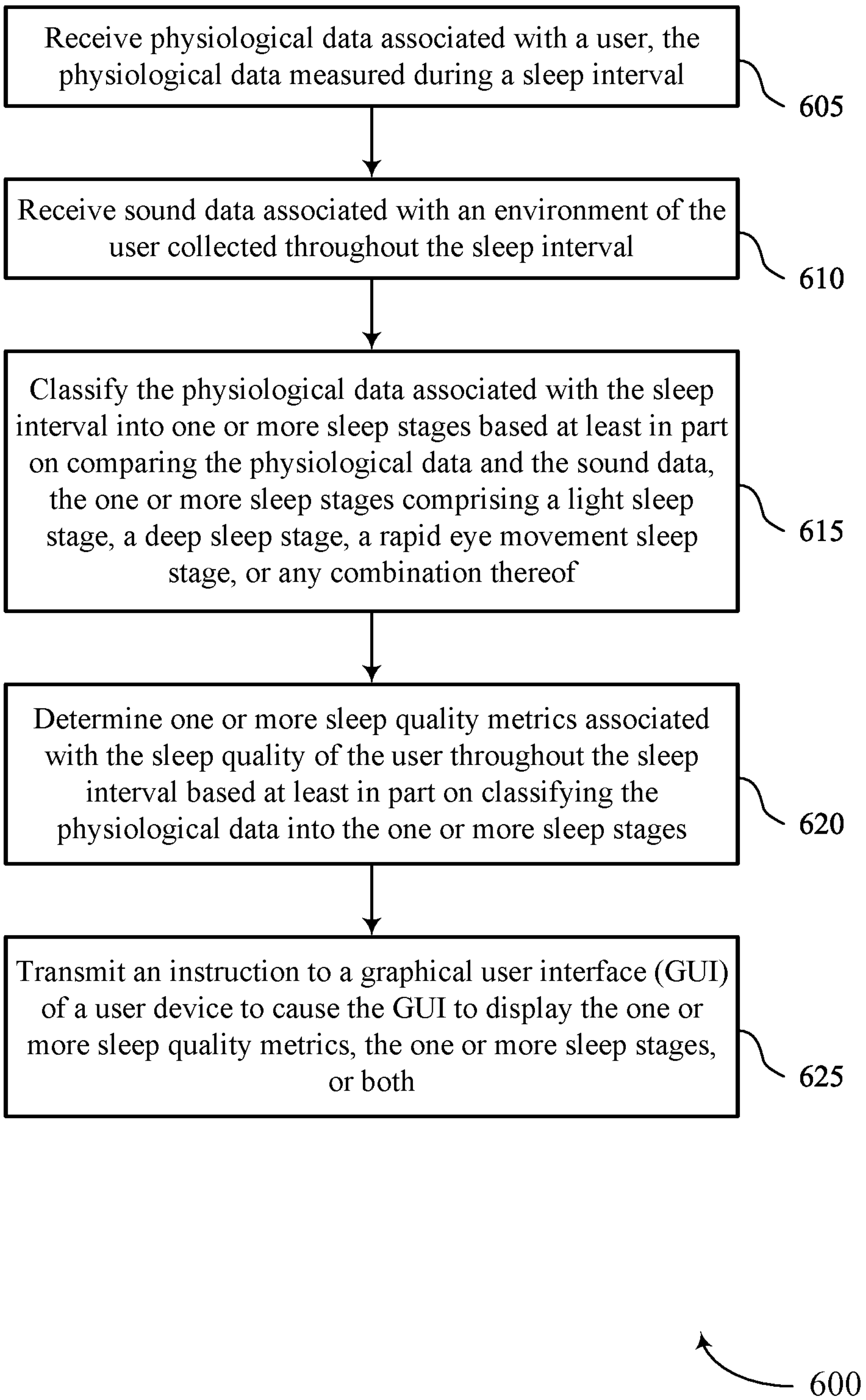
FIG. 6 shows a flowchart illustrating methods that support detection of snoring and environmental sounds in accordance with aspects of the present disclosure.

FIG. 6 shows a flowchart illustrating a method 600 that supports the detection of snoring and environmental sounds in accordance with aspects of the present disclosure. The operations of the method 600 may be implemented by or its components as described herein. For example, the operations of the method 600 may be performed by. In some examples, may execute a set of instructions to control the functional elements of to perform the described functions. Additionally, or alternatively, may perform aspects of the described functions using special-purpose hardware.

At 605, the method may include receiving physiological data associated with a user, the physiological data measured during a sleep interval. The operations of block 605 may be performed in accordance with examples as disclosed herein.

At 610, the method may include receiving sound data associated with an environment of the user collected throughout the sleep interval. The operations of block 610 may be performed in accordance with examples as disclosed herein.

At 615, the method may include classifying the physiological data associated with the sleep interval into one or more sleep stages based at least in part on comparing the physiological data and the sound data, the one or more sleep stages comprising a light sleep stage, a deep sleep stage, a REM sleep stage, or any combination thereof. The operations of block 615 may be performed in accordance with examples as disclosed herein.

At 620, the method may include determining one or more sleep quality metrics associated with the sleep quality of the user throughout the sleep interval based at least in part on classifying the physiological data into the one or more sleep stages. The operations of block 620 may be performed in accordance with examples as disclosed herein.

At 625, the method may include transmitting an instruction to a GUI of a user device to cause the GUI to display the one or more sleep quality metrics, the one or more sleep stages, or both. The operations of block 625 may be performed in accordance with examples as disclosed herein.

It should be noted that the methods described above describe possible implementations, and that the operations and the steps may be rearranged or otherwise modified and that other implementations are possible. Furthermore, aspects from two or more of the methods may be combined.

A method for evaluating a sleep quality of a user using wearable-based data by an apparatus is described. The method may include receiving physiological data associated with a user, the physiological data measured during a sleep interval, receiving sound data associated with an environment of the user collected throughout the sleep interval, classifying the physiological data associated with the sleep interval into one or more sleep stages based at least in part on comparing the physiological data and the sound data, the one or more sleep stages comprising a light sleep stage, a deep sleep stage, a REM sleep stage, or any combination thereof, determining one or more sleep quality metrics associated with the sleep quality of the user throughout the sleep interval based at least in part on classifying the physiological data into the one or more sleep stages, and transmitting an instruction to a GUI of a user device to cause the GUI to display the one or more sleep quality metrics, the one or more sleep stages, or both.

An apparatus for evaluating a sleep quality of a user using wearable-based data is described. The apparatus may include one or more memories storing processor executable code, and one or more processors coupled with the one or more memories. The one or more processors may individually or collectively operable to execute the code to cause the apparatus to receive physiological data associated with a user, the physiological data measured during a sleep interval, receive sound data associated with an environment of the user collected throughout the sleep interval, classify the physiological data associated with the sleep interval into one or more sleep stages based at least in part on comparing the physiological data and the sound data, the one or more sleep stages comprising a light sleep stage, a deep sleep stage, a REM sleep stage, or any combination thereof, determine one or more sleep quality metrics associated with the sleep quality of the user throughout the sleep interval based at least in part on classifying the physiological data into the one or more sleep stages, and transmit an instruction to a GUI of a user device to cause the GUI to display the one or more sleep quality metrics, the one or more sleep stages, or both.

Another apparatus for evaluating a sleep quality of a user using wearable-based data is described. The apparatus may include means for receiving physiological data associated with a user, the physiological data measured during a sleep interval, means for receiving sound data associated with an environment of the user collected throughout the sleep interval, means for classifying the physiological data associated with the sleep interval into one or more sleep stages based at least in part on comparing the physiological data and the sound data, the one or more sleep stages comprising a light sleep stage, a deep sleep stage, a REM sleep stage, or any combination thereof, means for determining one or more sleep quality metrics associated with the sleep quality of the user throughout the sleep interval based at least in part on classifying the physiological data into the one or more sleep stages, and means for transmitting an instruction to a GUI of a user device to cause the GUI to display the one or more sleep quality metrics, the one or more sleep stages, or both.

A non-transitory computer-readable medium storing code for evaluating a sleep quality of a user using wearable-based data is described. The code may include instructions executable by a processor to receive physiological data associated with a user, the physiological data measured during a sleep interval, receive sound data associated with an environment of the user collected throughout the sleep interval, classify the physiological data associated with the sleep interval into one or more sleep stages based at least in part on comparing the physiological data and the sound data, the one or more sleep stages comprising a light sleep stage, a deep sleep stage, a REM sleep stage, or any combination thereof, determine one or more sleep quality metrics associated with the sleep quality of the user throughout the sleep interval based at least in part on classifying the physiological data into the one or more sleep stages, and transmit an instruction to a GUI of a user device to cause the GUI to display the one or more sleep quality metrics, the one or more sleep stages, or both.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A system for evaluating a sleep quality of a user using wearable-based data, comprising:

a wearable device configured to measure physiological data associated with the user during a sleep interval;

an audio recording component configured to acquire sound data associated with an environment of the user collected during the sleep interval; and one or more processors communicatively coupled with the wearable device and the audio recording component, the one or more processors configured to:

receive the physiological data measured from the user;

receive the sound data associated with the environment of the user collected throughout the sleep interval, the sound data comprising one or more sound instances occurring throughout the sleep interval;

classify the one or more sound instances with one or more labels corresponding to the one or more sound instances;

classify the physiological data associated with the sleep interval into one or more sleep stages based at least in part on comparing the physiological data and the sound data, the one or more sleep stages comprising a light sleep stage, a deep sleep stage, a rapid eye movement sleep stage, or any combination thereof;

determine one or more sleep quality metrics associated with the sleep quality of the user throughout the sleep interval based at least in part on classifying the physiological data into the one or more sleep stages;

transmit an instruction to a graphical user interface (GUI) of a user device to cause the GUI to display the one or more sleep quality metrics, the one or more sleep stages, an indication of the one or more sound instances, or any combination thereof;

receive, from the user device, a user input indicating an updated label to replace a first label associated with a first sound instance of the one or more sound instances; and transmit a second instruction to cause the GUI of the user device to display the updated label.

2. The system of claim 1, wherein the one or more processors are further configured to:

identify the one or more sound instances within the sound data occurring throughout the sleep interval; and identify one or more transitions between the one or more sleep stages based at least in part on identifying the one or more sound instances, wherein classifying the physiological data into the one or more sleep stages is based at least in part on identifying the one or more transitions.

3. The system of claim 1, wherein the one or more processors are further configured to:

determine a change in one or more metrics of the physiological data during a time instance of the sleep interval; and classify one or more sounds within a portion of the sound data corresponding to the time instance as a snoring instance based at least in part on the change in the one or more metrics, wherein the instruction to the GUI of the user device causes the GUI to display information associated with the snoring instance.

4. The system of claim 3, wherein the change in the one or more metrics comprises a decrease in an oxygen saturation level.

5. The system of claim 1, wherein the one or more processors are further configured to:

identify a plurality of snoring instances associated with the user during the sleep interval; and adjust the one or more sleep quality metrics based at least in part on a quantity of snoring instances within the plurality of snoring instances.

6. The system of claim 1, wherein the one or more processors are further configured to:

transmit at least a portion of the sound data associated with the one or more sound instances to the user device to cause the user device to support playback of the one or more sound instances, wherein receiving the user input indicating the updated label is based at least in part on transmitting the portion of the sound data.

7. The system of claim 6, wherein, for each respective sound instance of the one or more sound instances, the second instruction causes the GUI to display a button associated with playback of the respective sound instance.

8. The system of claim 1, wherein, to classify the one or more sound instances with the one or more labels, the one or more processors are further configured to:

generate a spectrogram associated with a sound instance of the one or more sound instances;

compare the spectrogram with a plurality of sample spectrograms associated with a plurality of sample sounds included within a sound bank, the plurality of sample sounds corresponding to a plurality of labels; and obtain a label for the sound instance based at least in part on matching the spectrogram with a sample spectrogram corresponding to the label.

9. The system of claim 1, wherein the one or more labels comprise a snoring label, a coughing label, a breathing label, a talking label, a pet label, a children label, a movement label, a footsteps label, a sneezing label, an alarm clock label, a thunderstorm label, an unclassified label, or a combination thereof.

10. The system of claim 1, wherein the one or more processors are further configured to:

determine that the user has fallen asleep based at least in part on physiological data collected by the wearable device; and transmit a second instruction to cause the audio recording component to begin acquiring the sound data for the sleep interval based at least in part on determining that the user has fallen asleep.

11. The system of claim 1, wherein the one or more processors are further configured to:

determine that the user has awakened from the sleep interval based at least in part on the physiological data; and transmit a third instruction to cause the audio recording component to cease acquiring the sound data based at least in part on determining that the user has awakened.

12. The system of claim 1, wherein the one or more processors are further configured to:

receive, from the user device, a user input to initiate sound recording of the environment; and transmit a second instruction to cause the audio recording component to acquire the sound data based at least in part on receiving the user input, wherein receiving the sound data is based at least in part on receiving the user input, transmitting the second instruction to the audio recording component, or both.

13. The system of claim 12, wherein the one or more processors are further configured to:

receive, from the user device, a second user input to cease sound recording of the environment; and transmit a third instruction to the audio recording component to terminate acquisition of the sound data based at least in part on receiving the second user input to cease sound recording of the environment.

14. The system of claim 1, wherein the one or more processors are further configured to:

determine a first fundamental frequency associated with a first set of snoring instances within the sound data;

determine a second fundamental frequency associated with a second set of snoring instances within the sound data; and classify the first set of snoring instances as snoring of the user and the second set of snoring instances as snoring of a second user based at least in part on determining the first fundamental frequency and the second fundamental frequency.

15. The system of claim 1, wherein the one or more processors are further configured to:

determine a volume of one or more sound instances within the sound data; and adjust a sleep quality metric of the one or more sleep quality metrics based at least in part on the volume of the one or more sound instances.

16. The system of claim 1, wherein the audio recording component comprises a component of the wearable device, or a component of a charger device configured to charge the wearable device when the wearable device is mounted on the charger device.

17. The system of claim 1, wherein classifying the physiological data associated with the sleep interval into the one or more sleep stages is based at least in part on a breathing volume of the sound data, a quantity of movement instances detected by the wearable device, a quantity of sound instances within the sound data, or any combination thereof.

18. A method for evaluating a sleep quality of a user using wearable-based data, comprising:

receiving physiological data associated with a user, the physiological data measured during a sleep interval;

receiving sound data associated with an environment of the user collected throughout the sleep interval, the sound data comprising one or more sound instances occurring throughout the sleep interval;

classifying the one or more sound instances with one or more labels corresponding to the one or more sound instances;

classifying the physiological data associated with the sleep interval into one or more sleep stages based at least in part on comparing the physiological data and the sound data, the one or more sleep stages comprising a light sleep stage, a deep sleep stage, a rapid eye movement sleep stage, or any combination thereof;

determining one or more sleep quality metrics associated with the sleep quality of the user throughout the sleep interval based at least in part on classifying the physiological data into the one or more sleep stages;

transmitting an instruction to a graphical user interface (GUI) of a user device to cause the GUI to display the one or more sleep quality metrics, the one or more sleep stages, an indication of the one or more sound instances, or any combination thereof;

receiving, from the user device, a user input indicating an updated label to replace a first label associated with a first sound instance of the one or more sound instances; and transmitting a second instruction to cause the GUI of the user device to display the updated label.

* * * * *